United States Patent
Snitkin et al.

(10) Patent No.: US 7,025,063 B2
(45) Date of Patent: Apr. 11, 2006

(54) COATED SLING MATERIAL

(75) Inventors: Eva S. Snitkin, Minneapolis, MN (US); John W. Westrum, Jr., Prior Lake, MN (US); James E. Cabak, Plymouth, MN (US)

(73) Assignee: AMS Research Corporation, Minnetonka, MN (US)

( * ) Notice: Subject to any disclaimer, the term of this patent is extended or adjusted under 35 U.S.C. 154(b) by 715 days.

(21) Appl. No.: 09/939,098

(22) Filed: Aug. 24, 2001

(65) Prior Publication Data

US 2002/0072694 A1 Jun. 13, 2002

Related U.S. Application Data

(60) Provisional application No. 60/230,647, filed on Sep. 7, 2000.

(51) Int. Cl.
*A61F 5/48* (2006.01)
*A61F 2/02* (2006.01)
*A61F 2/00* (2006.01)

(52) U.S. Cl. .................... 128/885; 600/30; 600/37

(58) Field of Classification Search ......... 604/329–331; 600/29–31, 37; 128/885, 886
See application file for complete search history.

(56) References Cited

U.S. PATENT DOCUMENTS

| | | |
|---|---|---|
| 3,789,828 A | 2/1974 | Schulte |
| 4,128,100 A | 12/1978 | Wendorff |
| 4,235,238 A | 11/1980 | Ogiu et al. |
| 4,347,847 A | 9/1982 | Usher |

(Continued)

FOREIGN PATENT DOCUMENTS

| | | |
|---|---|---|
| DE | 196 13 317 A | 10/1996 |
| EP | 0 159 502 A | 10/1985 |
| EP | 0 265 157 A | 4/1988 |
| EP | 537769 | 10/1992 |
| EP | 647439 | 9/1994 |
| EP | 797962 | 3/1997 |
| EP | 0621014 | 8/2000 |
| FR | 2 737 106 A | 1/1997 |

(Continued)

OTHER PUBLICATIONS

Bryans, Fred E., Marlex Gauze Hammock Sling Operation with Cooper's Ligament Attachment in the Management of Recurrent Urinary Stress Incontinence, American Journal of Obstetrics and Gynecology, vol. 133, pp. 292–294.

Choe, Jong M. et al., Gore–Tex Patch Sling: 7 Years Later, Urology, vol. 54, pp. 641–646 (1999).

Falconer, C. et al., Clinical Outcome and Changes in Connective Tissue Metabolism After Intravaginal Slingplasty in Stress Incontinence Women, International Urogynecology Journal, pp. 133–137 (1966).

(Continued)

*Primary Examiner*—Weilun Lo
*Assistant Examiner*—C. Lynne Anderson
(74) *Attorney, Agent, or Firm*—Jeffrey J. Hobenshell

(57) ABSTRACT

The present invention relates to a sling, methods of making and using a sling, and kits comprising a sling for treating urinary incontinence. The sling has multiple elongation properties that serve to improve the support of the urethra. The sling may comprise a coated material adapted for urethral suspension. The coated sling has properties that appear to enhance the sling elongation characteristics. The coated sling further includes properties that reduce its susceptibility to bacterial infections. The sling further includes properties to enhance the proper tensioning of the sling.

18 Claims, 7 Drawing Sheets

U.S. PATENT DOCUMENTS

| | | |
|---|---|---|
| 4,403,604 A * | 9/1983 | Wilkinson et al. ............ 600/37 |
| 4,441,497 A | 4/1984 | Paudler |
| 4,509,516 A | 4/1985 | Richmond |
| 4,520,821 A | 6/1985 | Schmidt et al. |
| 4,655,221 A | 4/1987 | Devereux |
| 4,769,038 A | 9/1988 | Bendavid et al. |
| 4,775,380 A | 10/1988 | Seedhom et al. |
| 4,865,031 A | 9/1989 | O'Keeffe |
| 4,938,760 A | 7/1990 | Burton et al. |
| 4,941,466 A | 7/1990 | Romano |
| 4,946,467 A | 8/1990 | Ohi et al. |
| 4,969,892 A | 11/1990 | Burton et al. |
| 5,013,292 A | 5/1991 | Lemay |
| 5,026,398 A | 6/1991 | May et al. |
| 5,032,508 A | 7/1991 | Naughton et al. |
| 5,080,664 A | 1/1992 | Jain |
| 5,112,344 A | 5/1992 | Petros |
| 5,147,387 A | 9/1992 | Jansen et al. |
| 5,209,756 A | 5/1993 | Seedhom et al. |
| 5,222,987 A | 6/1993 | Jones |
| 5,250,033 A | 10/1993 | Evans et al. |
| 5,281,237 A | 1/1994 | Gimpelson |
| 5,290,217 A | 3/1994 | Campos |
| 5,292,328 A | 3/1994 | Hain et al. |
| 5,328,077 A | 7/1994 | Lou |
| 5,330,479 A | 7/1994 | Whitmore |
| 5,360,628 A | 11/1994 | Butland |
| 5,362,294 A | 11/1994 | Seitzinger |
| 5,368,595 A | 11/1994 | Lewis |
| 5,383,904 A | 1/1995 | Totakura et al. |
| 5,403,328 A | 4/1995 | Shallman |
| 5,441,508 A | 8/1995 | Gazielly et al. |
| 5,456,711 A | 10/1995 | Hudson |
| 5,509,918 A | 4/1996 | Romano |
| 5,520,700 A | 5/1996 | Beyar et al. |
| 5,569,273 A | 10/1996 | Titone et al. |
| 5,593,441 A | 1/1997 | Lichtenstein et al. |
| 5,611,515 A | 3/1997 | Benderev et al. |
| 5,624,704 A | 4/1997 | Darouiche et al. |
| 5,628,756 A | 5/1997 | Barker, Jr. et al. |
| 5,657,648 A | 8/1997 | Ives et al. |
| 5,658,307 A | 8/1997 | Exconde |
| 5,674,247 A | 10/1997 | Sohn |
| 5,681,325 A | 10/1997 | Hasson |
| 5,697,978 A | 12/1997 | Sgro |
| 5,738,628 A | 4/1998 | Sierocuk et al. |
| 5,756,145 A | 5/1998 | Darouiche |
| 5,807,403 A | 9/1998 | Beyar et al. |
| 5,836,503 A | 11/1998 | Ehrenfels et al. |
| 5,840,011 A | 11/1998 | Landgrebe et al. |
| 5,842,478 A | 12/1998 | Benderev et al. |
| 5,853,745 A | 12/1998 | Darouiche |
| 5,860,425 A | 1/1999 | Benderev et al. |
| 5,873,891 A | 2/1999 | Sohn |
| 5,899,909 A | 5/1999 | Claren et al. |
| 5,902,283 A | 5/1999 | Darouiche et al. |
| 5,922,026 A | 7/1999 | Chin |
| 5,934,283 A | 8/1999 | Willem et al. |
| 5,935,122 A | 8/1999 | Fourkas et al. |
| 5,945,422 A | 8/1999 | Doherty et al. |
| 5,972,000 A | 10/1999 | Beyar et al. |
| 6,010,447 A * | 1/2000 | Kardjian ............ 600/29 |
| 6,039,686 A | 3/2000 | Kovac |
| 6,042,534 A | 3/2000 | Gellman et al. |
| 6,042,536 A | 3/2000 | Tihon et al. |
| 6,042,592 A | 3/2000 | Schmitt |
| 6,045,571 A | 4/2000 | Hill et al. |
| 6,068,591 A | 5/2000 | Bruckner et al. |
| 6,074,341 A | 6/2000 | Anderson et al. |
| 6,090,116 A | 7/2000 | D'Aversa et al. |
| 6,099,547 A | 8/2000 | Gellman et al. |
| 6,110,101 A | 8/2000 | Tihon et al. |
| 6,117,067 A | 9/2000 | Gil-Vernet |
| 6,120,539 A | 9/2000 | Eldridge et al. |
| 6,162,487 A | 12/2000 | Darouiche |
| 6,162,962 A | 12/2000 | Hinsch et al. |
| 6,183,499 B1 | 2/2001 | Fischer et al. |
| 6,221,005 B1 * | 4/2001 | Bruckner et al. ............ 600/30 |
| 6,264,702 B1 | 7/2001 | Ory et al. |
| 6,273,852 B1 | 8/2001 | Lehe et al. |
| 6,306,079 B1 * | 10/2001 | Trabucco ............ 600/30 |
| 6,368,859 B1 * | 4/2002 | Atala ............ 435/395 |
| 6,451,032 B1 | 9/2002 | Ory et al. |
| 6,478,727 B1 | 11/2002 | Scetbon |
| 6,491,703 B1 | 12/2002 | Ulmsten |
| 2001/0018549 A1 | 8/2001 | Scetbon |
| 2002/0099260 A1 | 7/2002 | Suslian |
| 2002/0138025 A1 | 9/2002 | Gellman et al. |
| 2003/0004395 A1 | 1/2003 | Therin |
| 2003/0036676 A1 | 2/2003 | Scetbon |

FOREIGN PATENT DOCUMENTS

| | | |
|---|---|---|
| WO | 92/06638 | 4/1992 |
| WO | 93/17635 | 9/1993 |
| WO | 96/03091 A1 | 2/1996 |
| WO | 96/03165 A1 | 2/1996 |
| WO | WO 96/40307 | 12/1996 |
| WO | 97/47246 | 12/1997 |
| WO | 98/14134 | 4/1998 |
| WO | 98/31301 | 7/1998 |
| WO | 98/49967 | 11/1998 |
| WO | WO 98/58598 A | 12/1998 |
| WO | 00/27304 | 5/2000 |
| WO | 00/57812 | 10/2000 |
| WO | 00/64370 | 11/2000 |
| WO | 00/74578 A2 | 12/2000 |
| WO | 00/74594 A1 | 12/2000 |
| WO | 01/39670 A1 | 6/2001 |
| WO | WO 02/49095 | 7/2001 |
| WO | WO 01/56499 | 8/2001 |
| WO | WO 02/19944 | 3/2002 |
| WO | WO 02/28312 A | 4/2002 |
| WO | WO 02/30482 | 4/2002 |
| WO | WO 02/32284 | 4/2002 |
| WO | WO 02/38079 | 5/2002 |
| WO | WO 02/39890 | 5/2002 |
| WO | WO 02/064184 | 8/2002 |
| WO | WO 02/069781 | 9/2002 |
| WO | WO 02/087468 | 11/2002 |
| WO | WO 02/091950 | 11/2002 |

OTHER PUBLICATIONS

Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648–652 (Apr. 1998).

Kersey, J., The Gauze Hammock Sling Operation in the Treatment of Stress Incontintence, British Journal of Obstetrics and Gynaecology, vol. 90, pp. 945–949 (Oct. 1983).

Kluthe, John M.D. et al, The promise of tension–free vaginal tape for female SUI, Contemporary Urology, 7 pages (Oct. 2000).

Korda, A. et al., Experience with Silastic Slings for Female Urinary Incontinence, Aust NZ J. Obstet Gynaecol, vol. 29, pp. 150–154 (May 1989).

Kovac, S. Robert, et al, Pubic Bone Suburethral Stabilization Sling for Recurrent Urinary Incontinence, Obstetrics & Gynecology, vol. 89, No. 4, pp. 624–627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow–up of the Pubic Bone Suburethral Stabilization Sling Operation for Recurrent Urinary Incontinence (Kovac Procedure), Journal of Pelvic Surgery, pp. 156–160 (May 1999).

Leach, Gary E., et al., Female Stress Urinary Incontinence Clinical Guidelines Panel Report on Surgical Management of Female Stress Urinary Incontinence, American Urological Association, vol. 158, pp. 875–880 (Sep. 1997).

McGuire, Edward J. et al., Experience with Pubovaginal Slings for Urinary Incontinence at the University of Michigan, Journal of Urology, vol. 138, pp. 90–93 (1987).

Morgan, J. E., A Sling Operation, Using Marlex Polypropylene Mesh, for the Treatment of Recurrent Stress Incontinence, Am. J. Obst. & Gynecol, pp. 369–377 (Feb. 1970).

Morgan, J. E. et al., The Marlex Sling Operation for the Treatment of Recurrent Stress Urinary Incontinence: A 16–Year Review, American Obstetrics Gynecology, vol. 151, No. 2, pp. 224–226 (Jan. 1998).

Norris, Jeffrey P. et al., Use of Synthetic Material in Sling Surgery: A Minimally Invasive Approach, Journal of Endourology, vol. 10, pp. 227–230 (Jun. 1996).

Rackley, Raymond R. et al., Tension–Free Vaginal Tape and Percutaneous Vaginal Tape Sling Procedures, Techniques in Urology, vol. 7, No. 2, pp. 90–100 (2001).

Rackley, Raymond R. M.D., Synthetic Slings: Five Steps for Successful Placement, Urology Times, p. 46,48,49 (Jun. 2000).

Raz, Shlomo, Female Urology, pp. 80–86, 369–398, 435–442 (1996).

Staskin, David R. et al., The Gore–Tex Sling Procedure for Female Sphincteric Incontinence: Indications, Technique, and Results, World Journal of Urology, vol. 15, pp. 295–299 (1997).

Ulmsten, U. et al., An Ambulatory Surgical Procedure Under Local Anesthesia for Treatment of Female Urinary Incontinence, International Urogynecology Journal, vol. 7, pp 81–86 (May 1996).

Ulmsten, U. et al., Intravaginal Slingplasty (IVS): An Ambulatory Surgical Procedure for Treatment of Remale Urinary Incontinence, Scandinavian Journal of Urology Nephrol 29, pp. 75–82 (1995).

Winters C. et al., Vaginal Surgery, Use of Bone Anchors in Female Urology, p. 13–22 (2000).

Massimo Diana, et al., The American Journal of Surgery, Treatment of Vaginal Vault Prolapse with Abdominal Sacral Colpopexy Using Prolene Mesh, vol. 179 p. 128 (Feb. 2000).

Costantini E., et al., European Urology, Colposacropexy with Gore–Tex Mesh in Marked Vaginal and Uterovaginal Prolapse, p. 111–117 (1998).

Lienemann Andreas, et al., Obstetrics & Gynecology, Functional Cine Magnetic Resonance Imaging in Women After Abdominal Sacrocolpopexy, p. 81–85 vol. 97, No. 1 (Jan. 2001).

Rackley Raymond, Urology Times, Synthetic Slings: Five Steps for Successful Placement, p. 47–49 (Jun. 2000).

TVT Tension–free Vaginal Tape, Gynecare, 6 pages (1999).

Ulmsten U et al., A Three–Year Follow Up of Tension Free Vaginal Tape for Surgical Treatment of Female Stress Urinary Incontinence, British Journal of Obstetrics and Gynaecology, vol. 106 p. 345–350 (1999).

Ulmsten U et al., Intravaginal Slingplasty (IVS): An Ambulatory Surgical Procedure for Treatment of Female Urinary Incontinence, Scand J Urol Nephrol 29: p. 75–82 (1995).

Nichols David, Sacrospinous Fixation for Massive Eversion of the Vagina, Am J. Obstet. Gynecol., p. 901–904 (Apr. 1, 1982).

Richter Kurt, Massive Eversion of the Vagina: Pathogenesis, Diagnosis, and Therapy of the "True" Prolapse of the Vaginal Stump, Clinical Obstetrics and Gyneocology, vol. 25 No. 4, p. 897–912 (Dec. 1982).

* cited by examiner

COATED SLING MATERIAL

This application claims priority to U.S. Provisional Patent Application No. 60/230,647, filed Sep. 7, 2000.

FIELD OF THE INVENTION

The present invention generally relates to the repair of tissue defects in a patient, including such defects as hernia. The present invention specifically relates to devices and methods in the long-term cure of recurrent female urinary incontinence. More particularly, the present invention relates to slings for use in treating female urinary incontinence and methods of making and using the slings.

BACKGROUND OF THE INVENTION

Normal urination and continence is dependent upon normal function of the urinary tract, kidneys and nervous system. In addition, in women, continence requires correct coaptation and urethral support. Specifically, in order for continence to be maintained, the urethra must be supported and stabilized in its normal anatomic position behind the pubic bone, adjacent to the vaginal wall. The natural support system for the female urethra is a layer of support composed of pelvic and vaginal wall tissue and ligaments, which attach to the pubic bone. Relaxation, weakening or loss of this support system results in hypermobility of the urethra and bladder to an unnaturally low position within the pelvis. This defect contributes to about 30% of incontinence in women.

One form of incontinence, referred to as stress incontinence, is an involuntary loss of urine that occurs with increased abdominal pressure such as with coughing, sneezing, laughing, or lifting. Urethral hypermobility may be a result of pregnancy (one reason why stress incontinence is common in women who have had multiple pregnancies), or may be due to pelvic prolapse. In pelvic prolapse, there is a protrusion or falling of the bladder, urethra, or rectal wall into the woman's vaginal space. Additionally, in women with low estrogen levels such as in post-menopausal females, stress incontinence is more likely to occur due to decreased vaginal muscle tone resulting from the loss of estrogen.

Approaches for treating female urinary incontinence vary and include methods directed at elevating the urethra or the bladder neck (upper region of the urethra) to return it to its normal anatomical position behind the pubic bone. These methods include needle suspension procedures and sling procedures. The needle suspension procedure is a commonly used procedure which involves placement of sutures in the support tissue (fascia) on either side of the displaced urethra and attaching these sutures to fixed sites such as bone and soft tissue. Therefore, a variety of devices have been developed to aid in the fixed attachment of the sutures to the support structures. A disadvantage with this approach, however, is that the tissue support structures being used for the urethra are themselves stretched or otherwise deficient, thereby, making them inefficient as support structures and a less effective solution.

Another approach for treating female incontinence is the sling procedure. In this procedure a sling is formed by taking a piece of human abdominal tissue (fascia) or a piece of synthetic material and using this as a platform to provide support and/or restore the urethra to its normal retropubic position. Slings made of biological tissue require either growing or harvesting autologous tissue or using processed cadaveric tissue. Therefore, these types of sling materials are sometimes undesirable in that they increase the expense, surgeon's time required and complexity of the procedure.

As an alternative to human tissue, prefabricated or synthetic slings have been developed for use in treating incontinence and are described, for example, in U.S. Pat. No. 6,042,534. These slings are said to offer improvements to the sling procedure for treating incontinence in that the synthetic slings are supplied to the physician in shapes and dimensions adapted for urethral stabilization. This eliminates the need for sizing of the sling material by the surgeon during surgery, which greatly reduces the time required for the surgical procedure.

Another example of a synthetic sling and system for use in treating incontinence is described in U.S. Pat. No. 6,039,686 issued Mar. 21, 2000 to Kovac. The sling system of Kovac involves stabilizing the urethra using a mesh sling having an innovative mesh suturing pattern that is secured in vivo by short sutures attached to the posterior/inferior (lower, back) portion of the pubic bone instead of the superior (upper) portion of the pubic bone as with other methods.

The tissue and mesh used in prior slings can be fabricated or obtained from a variety of materials and sources. There does not appear to be any attention given to configuring, creating or modifying these slings in a manner to provide optimal elongation characteristics to the support tissue. Particular elongation properties are desirable in some circumstances, such as when the amount of tension or support at the region immediately surrounding the bladder neck of the urethra is important.

Tissue ingrowth, infection resistance and capacity to erode surrounding tissue are also factors in sling designs. The specific effect of the elasticity of the sling on these factors is not known in great detail.

In view of the above, although improvements in surgical treatment of urinary incontinence have been made, there is a need to provide even more improved sling systems so as to further enhance reliability and to better respond to patient kinetics.

SUMMARY OF THE INVENTION

In view of the foregoing, it is an object of the present invention to provide a surgical sling that addresses the limitations and disadvantages associated with prior devices and systems, yet meets the needs of the user.

A further object of the invention is to provide a sling apparatus having distinct elongation properties along its length and its width and that minimizes the complexities of the placement procedure for the surgeon.

A further object of the invention is to provide a surgical sling fabricated such that it has one elongation property in one direction and a second elongation property in a second direction.

An additional object of the invention is to provide a coating to a sling material that contributes to appropriate elongation property, improves biocompatibility and inhibits or resists infection.

An additional object of the invention is to provide a method of making and using a multiple elongation sling system for treatment of urinary incontinence. The system can include a surgical sling having several distinct elongation properties and adapted to be passed under the urethra for supporting the urethra in its normal anatomic position. When inserted into a patient, the sling can also prevent abnormal urethral descent in a patient.

An additional object of the invention is to provide a sling material made from a mesh wherein the mesh is coated but contains open holes or pores to promote tissue in-growth.

An additional object of the invention is to provide a sling material that provides visual indicia to the user that is indicative of a particular tensioned state of the sling material.

The present invention includes coated slings and slings having certain physical and biologic characteristics that increase the overall effectiveness and comfort of the sling once implanted in vivo. Such systems also include slings that provide visual indicia to the user indicating when the sling has been manipulated into a desired state, e.g., into a desired tension.

DETAILED DESCRIPTION OF THE INVENTION

The present invention provides efficient and reliable slings for use in treating males and females. The sling is particularly suitable for pelvic floor reconstruction surgery and for treating urinary incontinence. The features of the invention as described herein provide a surgical sling having at least two different elongation characteristics along its surface area. In addition, the slings may be coated with, for example, a silicone coating. Such coating is believed to contribute to the desired elongation properties of the mesh, assist with ensuring biocompatibility, and provide a carrier for anti-microbial agents.

Figure 1:
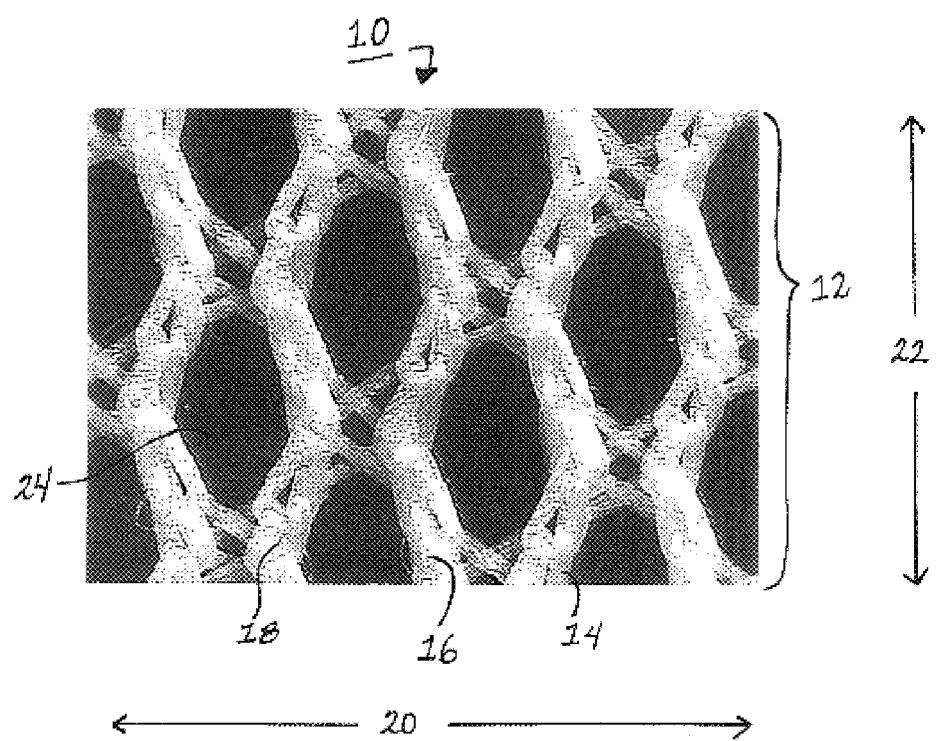
FIG. 1 is a view of an uncoated base material for use as a sling in accordance with one embodiment of the invention.

Referring to FIG. 1, an enlarged plan view of a material 10 according to one aspect of the invention includes a material that is a surgical mesh 12. Individual strands or filaments 14 collectively form a multifilament yarn 16 that can be woven or braided 18 to form the desired weave. The weave leads to a pattern of holes or pores 24.

Materials suitable for use in fabricating the coated slings of the present invention include man-made materials such as filamentous mesh materials. Filamentous mesh materials include synthetic fibers such as polyester, polyurethane, nylon, or polypropylene which can be woven or braided to form a mesh 12. The filaments in such materials may be oriented in a single direction or may be multidirectional.

As will be further described below, the pattern formed by the weave can be designed so as to provide a mesh material having directionally oriented elongation properties. In a preferred embodiment of the present invention, the mesh material comprises a weave pattern where the holes 24 have a diamond shape. As would be apparent to one skilled in the art, the degree of "stretch" or elongation properties in either direction of the mesh pattern can be adjusted as preferred by a user by altering the weave of the mesh material.

In a preferred embodiment, a synthetic filamentous material suitable for fabricating a mesh for use as a sling include a commercially available material comprised of a Rashel knit mesh made from 150 denier polyester yarn. Such a mesh has a hole size of approximately ¹⁄₃₂" (0.794 mm) and a weight of approximately 4.7 oz/yd. (133.25 gr/0.914 m). The yarn is a multi-filament yarn. In another embodiment a mesh know as Mersilene™ may be used.

The weave of the mesh according to one aspect of the invention is such that it has greater elongation properties in one direction 20 than it does in a second direction 22 transverse (or perpendicular) to the first direction 20.

In a preferred embodiment wherein the mesh is cut in a rectangular, sling-like configuration, the elongation properties of the mesh in the longitudinal direction are such that the mesh will elongate in the range of about 24%–28% beyond its normal state when placed in tension by a 20 lb. (9.072 kg) load. The elongation properties in a direction transverse (i.e., perpendicular) to the longitudinal direction, that is, in the latitudinal direction, are such that the mesh will elongate in the range of about 65%–75% beyond its normal state when placed in tension by a 20 lb. (9.072 kg) load.

By virtue of the longitudinal direction having lesser elongation properties than the latitudinal direction, there is less tendency for the longitudinal edges of the sling to curl in on themselves when the sling is in tension along the longitudinal direction. This is a desired property along the longitudinal direction of the mesh insofar as an implanted sling that becomes curled in this manner can be more prone to cause tissue irritation and ultimately tissue erosion in the patient.

Conversely, by virtue of the latitudinal direction of the mesh sling having greater elongation properties, the sling provides greater flexibility and "give" in a direction parallel to the urethra. As a result, the sling can still serve its function of treating incontinence but it does so with less trauma and greater comfort since the sling is now more responsive to patient movements and activities.

These desirable properties of the mesh are particularly acute in sling operations where the sling is attached to the pubic bone at the sling's opposite longitudinal ends. That is, the properties of the invention are best utilized when the sling is attached to opposite sides of the pubic bone and placed in tension along its longitudinal axis. In this manner, elongation is allowed in the longitudinal direction with minimal edge curling while at the same time the elongation is enhanced in the latitudinal direction to promote responsiveness to patient movement. This result is believed to make the sling procedure a more clinically stable procedure that improves patient comfort.

Alternatively, in some surgical procedures, the sling may be placed in the body in a tension free rest position. Even in this tension free rest position, the sling according to the present invention is believed to resist edge curling when anatomical movement (e.g. a stress event such as a cough) places tension on the sling.

As depicted in FIGS. 2A–3B, the present invention further contemplates a sling wherein the above-described mesh material is coated with a substance to enhance its properties and, in some cases, provide a platform for the impregnation of therapeutic substances (drugs, antibiotics, etc.). One such coating may be silicone. In particular, when the material of the sling is constructed of individual yarns that have the potential for tissue ingrowth, the silicone 30 substantially coats the exposed surfaces of the yarns and fills in irregular surfaces of the yarns of the mesh material and between individual yarns of the mesh, thereby substantially preventing in-growth of tissue into the fibers of the yarn of the sling material. Minimizing the exposed surface area also reduces the ability of bacteria or microbes to reside within the mesh material if the sling is exposed to bacteria during the implantation procedure. This is particularly advantageous as it decreases the risk of infection to the patient following implantation of the sling. This also restricts bacterial ingrowth into and between any fibers of the yarn, thereby further resisting infections.

As is evident from the figures, the coating is applied in a manner such that the holes or pores 24 of the mesh remain open and clear of silicone. That is, the exposed surfaces within the holes or pores 24 themselves remain open and free of silicone. As a result, a sling is obtained that resists infection (due to the coating) but also promotes tissue in-growth (due to the holes or pores 24).

A synthetic sling fabric material that is coated with a substance such as silicone is also advantageous in that the coating can provide lubricating characteristics to the mesh that enables easier adjustment of the sling during the implantation procedure. Further, the silicone coating creates in the sling a composite structure of the fabric and the silicone that better interacts with the patient's tissue. The silicone also coats the yarn material to the degree that the yarn functions much like a monofilament. Such a monofilament is believed to be less prone to infection. It is also believed to lead to less erosion of the tissue.

A coating such as silicone provides a platform from which therapeutic substances like antibiotics or antimicrobial agents can be introduced to the patient. Such agents can be impregnated into the silicone coating or, alternatively, may be formulated with the composition comprising the silicone coating and applied during the coating procedure. In some embodiments, a silicone coating containing or impregnated with antibiotic agents may contain a drug that is formulated to be time-released. Examples of agents suitable for use include antibiotics and antimycotics such as, gentamicin, fungizone, rifampin or minocycline HCL. Other agents may also be incorporated in the silicone, such as, but not limited to antiseptic agents, radioopaque agents and other antimicrobial agents.

In a preferred embodiment of the invention, the coating of the sling will also impact the dual elongation properties of the sling. For example, the fabric mesh discussed previously, which is later coated with silicone, will result in a mesh that elongates in its longitudinal direction about 19.5%–21.5% beyond its normal state when placed in tension at about 20 lbs. (9.072 kg) of force. Conversely, the mesh elongates in its latitudinal direction about 120%–130% beyond its normal state when placed in tension at about 20 lbs. (9.072 kg) of force. This is a desired result insofar as elongation properties are tending to be enhanced in the latitudinal direction (to provide patient comfort) but are tending to be minimized in the longitudinal direction (to reduce any curling propensities).

In this preferred embodiment, the reduced elongation properties in the longitudinal direction are believed to have been achieved as a result of holding the mesh in tension in the longitudinal direction at the time the mesh was coated. In other words, it appears that pre-stretching, or at least pre-tensioning the mesh in the longitudinal direction during the coating process, led to the reduction in elongation properties in the longitudinal direction as compared to the elongation properties in the longitudinal direction in the uncoated mesh sling. As a result, it is contemplated as part of the invention, that, should it be desired to avoid reduction of the elongation properties in the longitudinal direction, the mesh should not be held in tension along the longitudinal direction and perhaps should be held free of tension altogether, or in uniform tension, or in tension along the latitudinal direction prior to silicone coating.

In this regard, a number of tests have been performed to more fully expand the explanation and implementation of the present invention. These tests involve the acquisition of data on the elongation properties of the sling according to how the sling has been processed with a silicone coating. The result of the tests are set forth in the following table.

TABLE A

| 5 Lb test load | Uncoated | Si Coated w/o Pre-Tension | Si Coated w/ Longitudinal Pre-Tension | Si Coated w/ Latitudinal Pre-Tension |
|---|---|---|---|---|
| Longitudinal Elongation | 8% | 5% | 2.5% | 10.5% |
| Latitudinal Elongation | 36% | N/A | 65% | 25% |

As is evident from the table, there were four types of slings that were tested, namely: (1) an uncoated sling; (2) a sling that was not held in tension while being coated with silicone; (3) a sling that was held in longitudinal tension while being coated with silicone; and, (4) a sling that was held in latitudinal tension while being coated with silicone. As is also evident from the table, each of the four slings were tested for respective elongation properties both in the longitudinal direction and the latitudinal direction. These tests were conducted using a 5 lb tension-loading device.

The resulting data is consistent with the elongation figures discussed previously. For example, when the sling is coated with silicone while under longitudinal tension, there is a dramatic decrease in longitudinal elongation properties in the resulting sling accompanied with a dramatic increase in latitudinal elongation properties in the sling as compared to the corresponding elongation properties of an uncoated sling. In addition, a sling coated with silicone under latitudinal tension leads to a sling having increased longitudinal elongation properties accompanied with reduced latitudinal elongation properties. As a result, it can be seen that desirable elongation properties that would otherwise not be available under normal conditions can be "locked" into the sling during the coating process.

Figure 5:
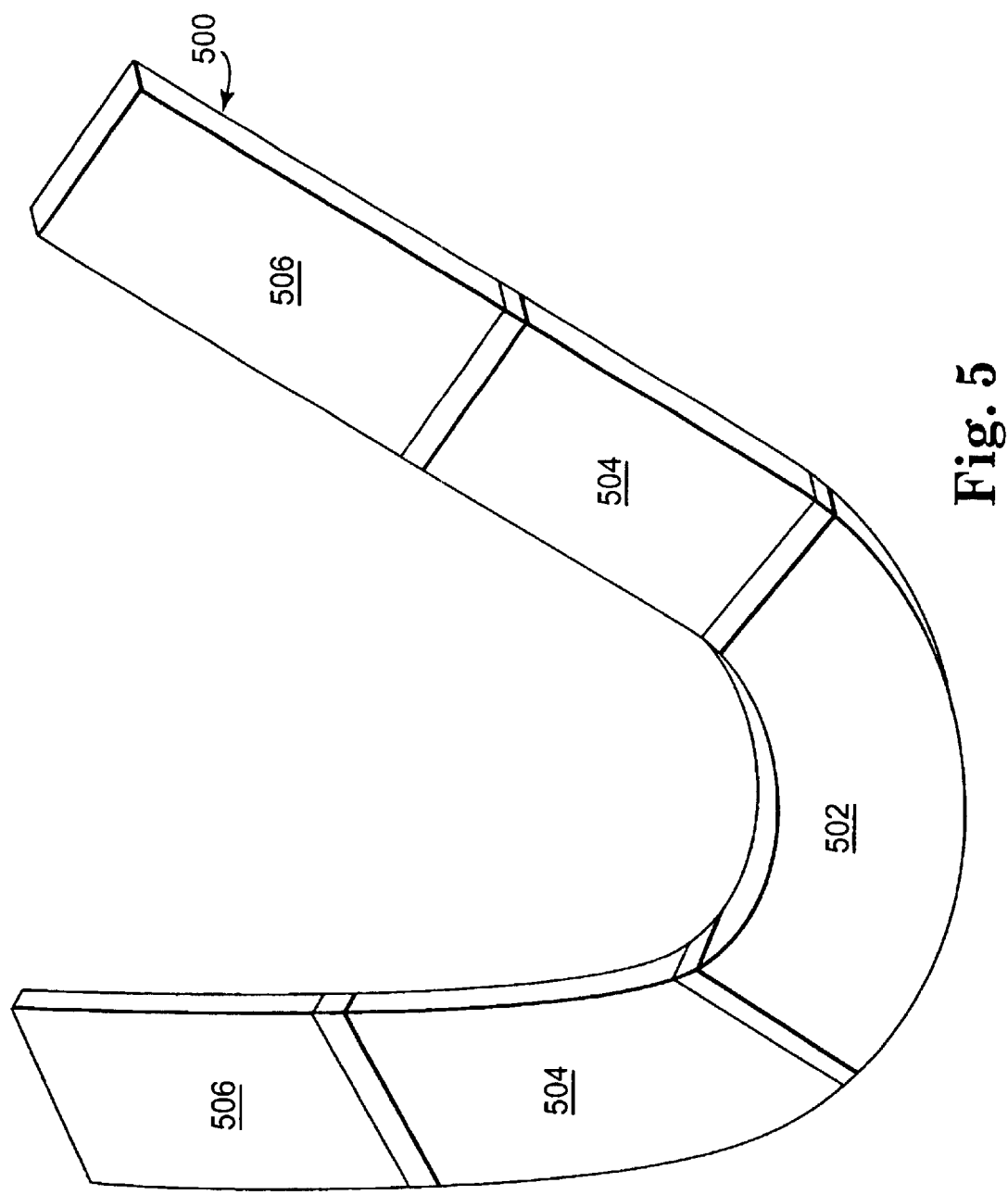
FIG. 5 is a schematic view of another preferred embodiment in accordance with the present invention.

One embodiment of the invention that is particularly exemplary of a manner in which to exploit the invention is set forth in FIG. 5. In this embodiment, a sling 500 is provided that has different elongation properties at different regions or zones on the sling. These regions are a result of molding separately manufactured strips or portions of coated fabric into a single sling 500.

For example, in one embodiment, the central region 502 of the sling 500 has been coated with silicone while in latitudinal tension thus giving this central region 502 a somewhat increased longitudinal elongation property and a somewhat decreased latitudinal elongation property over a non-pretensioned coated sling (see Table A).

The intermediate regions 504 of the sling 500 have been coated with silicone while in longitudinal pre-tension, thus giving the intermediate region 504 a dramatically decreased longitudinal elongation property and a dramatically increased latitudinal elongation property over a non-tensioned, coated sling. Moreover, the intermediate regions 504 may molded into place to form the sling in a transverse direction (i.e., rotated 90°) as compared to the configuration of the fabric in the central region 502. As a result the longitudinal and latitudinal elongation properties exhibited by these intermediate regions 504 of the sling 500 actually correspond to the latitudinal and longitudinal properties, respectively, set forth in Table A for the sling that was silicone coated while in longitudinal tension.

The end regions 506 of the sling 500 have been coated with silicone while in longitudinal tension thus giving the end regions 506 a decreased longitudinal elongation property and an increased latitudinal elongation property (see Table A). The end result is a sling 500 that provides varying elongation properties along the length of the sling 500 that can be best suited to mitigate undesirable curling tendencies of the sling while enhancing the desirable flexibility characteristics of the sling.

Although the aforesaid embodiment is disclosed as comprising discrete portions of coated fabric that are molded into a complete sling, this aspect of the invention is not so limited. For example, it is within the scope of the invention to create a similar "multi-zone" sling merely by coating various regions or zones of a unitary sling under differing tension parameters at these various regions or zones.

In view of the above disclosure, it will be seen that the dual elongation properties of the invention as well as the coating by a substance such as silicone, enhances and improves the efficiency of the sling when placed in the patient. Furthermore, the coating and method of coating improves the lubricity between the mesh and the tissue and also appears to enhance the elongation properties of the sling. In other words, a sling in accordance with the present invention provides the needed long term support for effectively stabilizing the urethra to its normal anatomical position while also permitting temporary movement of the urethra (due to the dynamic nature of the patient's anatomy and movements) with the pelvis.

Figure 2A:
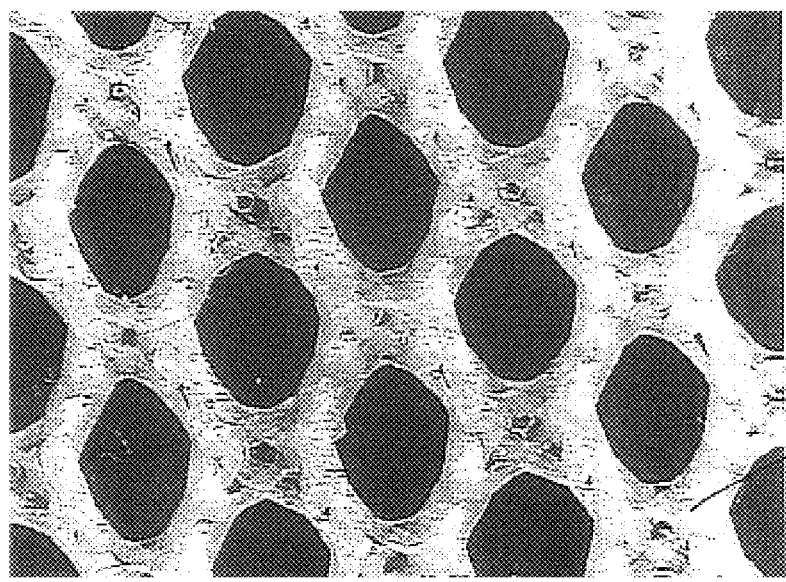
FIGS. 2A–2B are views of a first embodiment of a sling in accordance with the present invention.
Figure 2B:
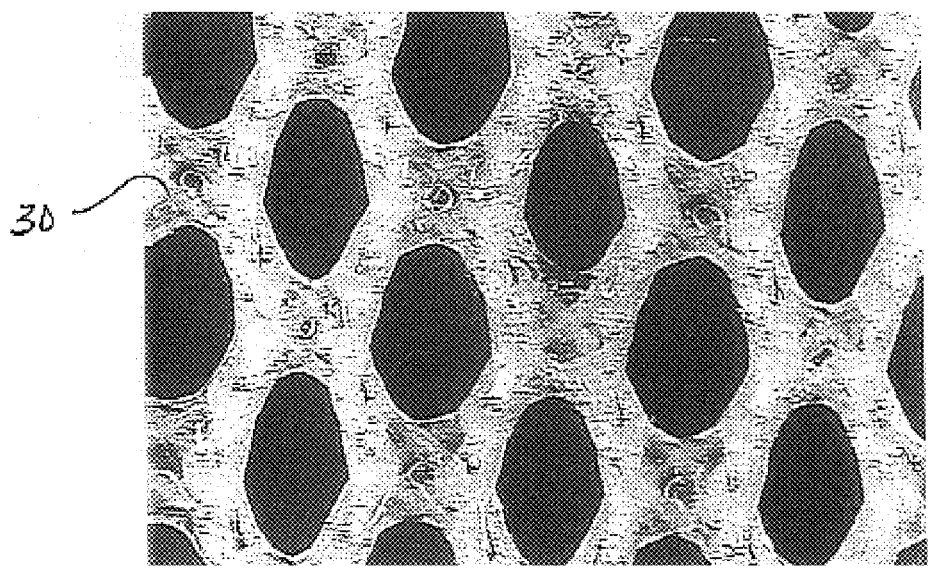
Figure 3A:
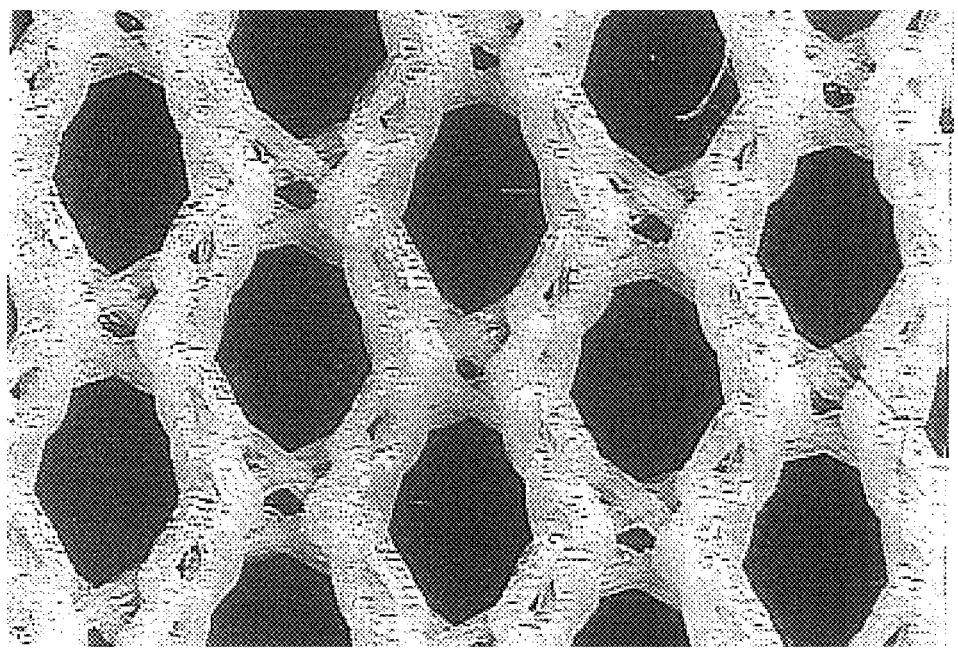
FIGS. 3A–3B are views of a second embodiment of a sling in accordance with the present invention.
Figure 3B:
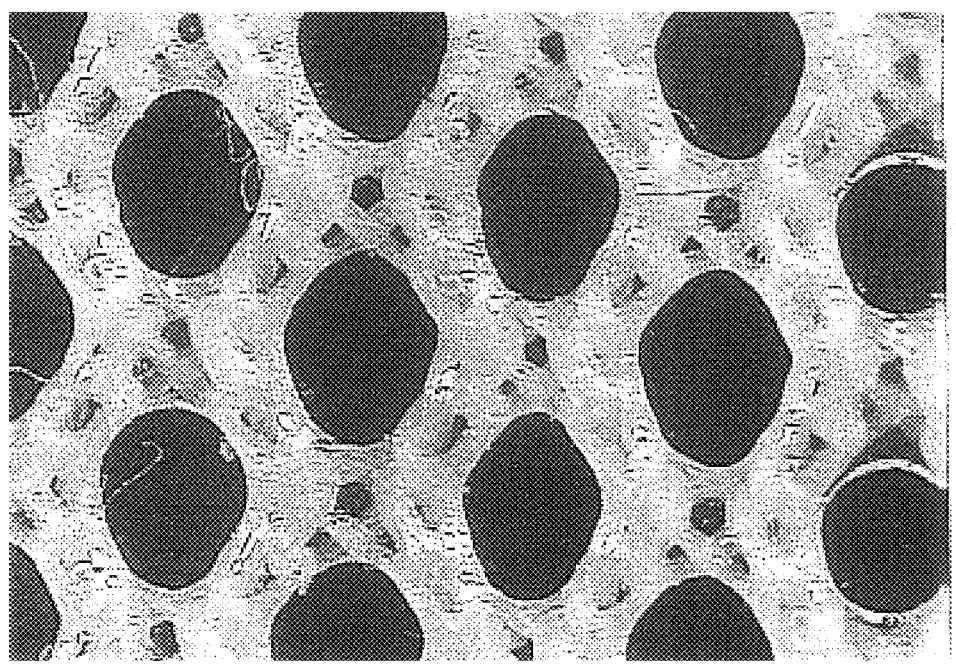

Depending upon the parameters of the coating process used, varying degrees of silicone thickness surrounding the mesh yarns can be obtained. However, in preferred embodiments, the holes or pores 24 remain open after coating. Referring to FIGS. 2A, 2B, 3A and 3B, depending upon the desire or need of the user, a sling can be coated so as to comprise a coated mesh material having a thickness ranging from about 0.024 inches (0.61 mm) to about 0.036 inches (0.914 mm) (FIGS. 3A, 3B) or from about 0.020 inches (0.508 mm) to about 0.025 inches (0.635 mm) (FIGS. 2A and 2B). In one embodiment, the thickness of the sling material in the uncoated state is about 0.020 inches (0.508 mm) plus or minus about 0.002 inches. In a preferred embodiment, the size of the holes or pores 24 after coating is preferably in the range of about 0.040 inches (1.016 mm) to about 0.055 inches (1.397 mm).

In a preferred embodiment, a silicone-coated sling will have a generally rectangular shape that is approximately 2–12 cm wide (more preferably 10 cm) and 5–20 cm long. In particular, a silicone-coated sling of the present invention will be of sufficient size and dimension so as to pass behind the urethra and support the urethra in its normal anatomic position when implanted in vivo. In addition, the silicone-coated sling should be adapted so as to be capable of preventing abnormal urethral descent under increased intra-abdominal pressure.

It is contemplated that the present invention can be used with a variety of sling systems and methods for treating urinary incontinence. For example, a coated sling in accordance with the present invention, can be used with the system for the long term cure of recurrent urinary female incontinence as described in co-pending U.S. Pat. No. 6,328,686, the entire disclosure of which is hereby incorporated by reference. When used in such a system, a silicone-coated sling can be installed in vivo using the vaginal installation procedure as described in the application. Alternatively, a coated sling in accordance with the present invention can be prefabricated according to the dimensions and shapes as described, for example, in U.S. Pat. No. 6,042,534 issued Mar. 28, 2000 entitled "Stabilization sling for use in minimally invasive pelvic surgery" and installed as described in U.S. Pat. No. 6,042,534. A coated sling of the present invention can also be installed abdominally or laparoscopically using procedures well known in the art.

In addition, sheets of silicone coated fabric may be prepared in a similar manner for general pelvic floor reconstruction.

Method for Silicone Coating a Sling

Figure 4:
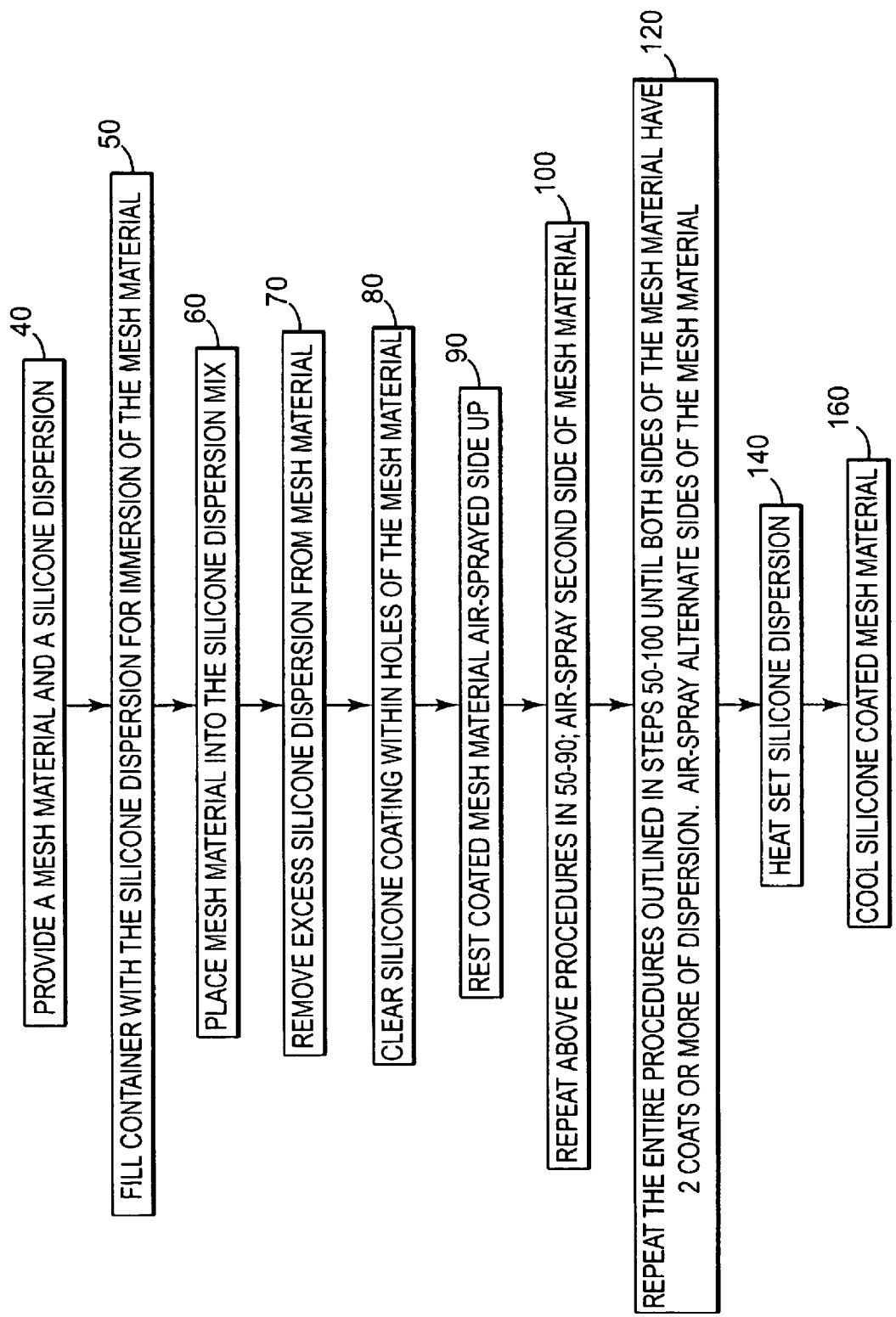
FIG. 4 is a flow chart for fabricating a sling in accordance with one embodiment of the invention.

FIG. 4 illustrates one preferred embodiment of a process of applying a silicone coat to a mesh material for use as a sling. The method includes step 40 of providing a mesh material which can be manipulated for use as a sling. In a preferred method, a silicone dispersion is selected for use as the coating material. In step 40, a preferred mesh material is as previously described. The silicone dispersion is preferably a medical grade silicone dispersion. The silicone dispersion is a result of mixing equal parts (100 g each) of a silicone such as Medium 6820 with 5 parts (500 g) solvent such as Xylene. The dispersion can be mixed by stirring on a stir plate in a fume hood. Mixing should be performed for a minimum of 20 minutes with the container covered so as to minimize evaporation.

Next, in step 50, a container such as an aluminum pan is filled with the silicone dispersion for immersion of the mesh material. The pan should be kept covered (with foil, for example) when not in use, so as to prevent evaporation.

In step 60, the mesh material is placed into the dispersion mix and is held flat by use of, for example, 6" (15.24 cm) embroidery hoops. When using embroidery hoops, the mesh material should be pulled through the edges of the hoop until the mesh material is taut, flat, and constrained along most if not all of the peripheral edges of the mesh material. Care should be taken not to inordinately stretch the material as this could result in distortion of the holes of the mesh material or in uneven coating of the mesh material, which can affect the dual elongation aspect of the sling. The mesh material should be trimmed to be sized closely to the dimensions of the hoop so as to minimize material overlap. The hoop containing the mesh material is placed into the pan containing the silicone dispersion for about 15 seconds, or more, and then removed.

In other embodiments, the sling material can be held in tension at opposite ends of the sheet prior to applying the coating. As discussed previously, depending on which direction of the mesh is in tension during coating, differing elongation properties in the sling may be obtained.

In step 70, excess silicone dispersion 42 is removed by allowing the silicone to drip off of the mesh material as the hoop is placed flat over the pan for about 1–5 minutes.

In step 80, the coating within the holes of the mesh material are cleared. This can be performed by using a foot-controlled air nozzle having an air setting of approximately 55-psi and 600 pulses per minute. Using the air nozzle, the coated mesh material can be continuously sprayed to clear the openings until there are minimal or no holes filled with silicone dispersion mix. In one embodiment, the spraying is performed intermittently. For example, pulsed air may be used.

In step 90, the coated mesh material is rested, air-sprayed side up, for approximately 5 to 15 minutes.

In step 100, the entire procedure outlined above in steps 50–90 is then repeated with the exception that the second side of the mesh material is now air-sprayed so as to ensure a uniform distribution of the silicone coating over all surfaces of the mesh material.

The spraying steps are performed also to ensure that the holes or pores of the mesh are not filled or closed with silicone. As stated previously in one embodiment of the invention, the sling has been coated with silicone but still contains open holes or pores to promote tissue growth.

In a preferred embodiment, the entire procedure outlined in steps 50–100 is repeated until both sides of the mesh material have 2 coats or more of dispersion 120. During the repeating process, alternate sides of the mesh material may be air-sprayed.

In step 140, the silicone coating is heated to set the silicone dispersion. This can be performed, for example, by hanging the hoops holding the mesh in an oven that is set at 160° C. (+/−10°) for about 20 minutes.

It is noted that the sling according to the present invention may be constructed using a batch process or a continuous process. For example, in a continuous process, the silicone dispersion may be placed in a large reservoir, and the strip material may be provided in an elongate, substantially continuous strip that is substantially continusously fed into the reservoir using, for example, rollers and/or mechanical clamping structures.

In step 160, the silicone coated mesh material is removed from the oven and allowed to cool. Following cooling, the material is then cut from the hoop. If desired, an antimicrobial substance or medicament can be impregnated into the silicone elastomer in a subsequent process.

After removing the material from the hoops, the silicone coated mesh material can then be fabricated as desired into a sling for use in treating urinary incontinence. As described previously, a silicone coated mesh material of the present invention, can be used to fabricate a sling such as described in U.S. Pat. No. 6,328,686, and then surgically implanted into a patient suffering from urinary incontinence.

In another embodiment, the sling material is configured in a long narrow elongated piece of mesh. The width is approximately the same width as a sling used in a patient. When coated, the edges of the material along the length of the material are coated with the silicone. When an elongated material is used in this manner, all that is required to obtain a sling suitable for use in a patient is to cut the elongated material through its width at the desired length of the sling. This will yield a sling that has the edges along the longitudinal side of the sling completely coated with silicone. In other words, since there is no necessary cutting in the longitudinal direction (because the material is already formulated to have the desired sling width) to obtain a desired size of sling, the integrity of the coating along the uncut edges remains intact, thus better ensuring the advantageous properties introduced in the sling as a result of coating.

A silicone coated sling as described herein can be fabricated into a variety of dimensions or can be manipulated to conform to a variety of sling specifications, depending upon user or manufacturer's preference. In addition, the coated sling can also be adapted so as to include structures to aid in the attachment or connection of the sling to the patient in vivo. It is also to be emphasized that silicone is only one coating that may be used, and, as such, is only exemplary, not limiting, in the context of the invention.

In still further embodiments in accordance with the present invention, it is desired to enable the user to more easily determine the presence and magnitude of tension in the sling material during placement of the sling. The ability to accurately make this determination will allow the user to adapt the fixation of the sling in the patient in a manner to maximize the potential of successfully treating the incontinence problem.

Figure 6A:
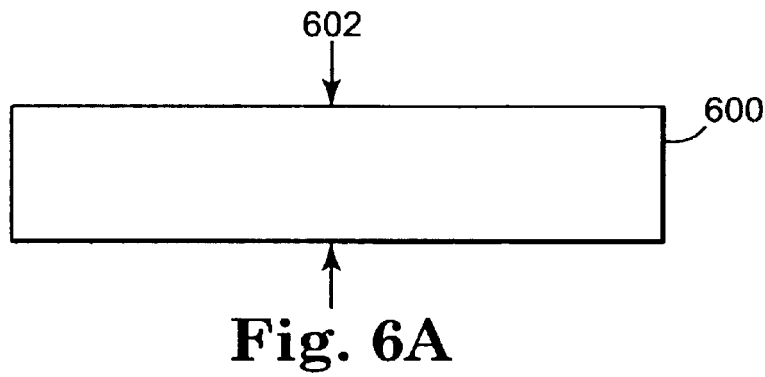
FIGS. 6A and 6B are views of a sling material in accordance with one embodiment of the present invention and a method of determining tension in accordance with the present invention.
Figure 6B:
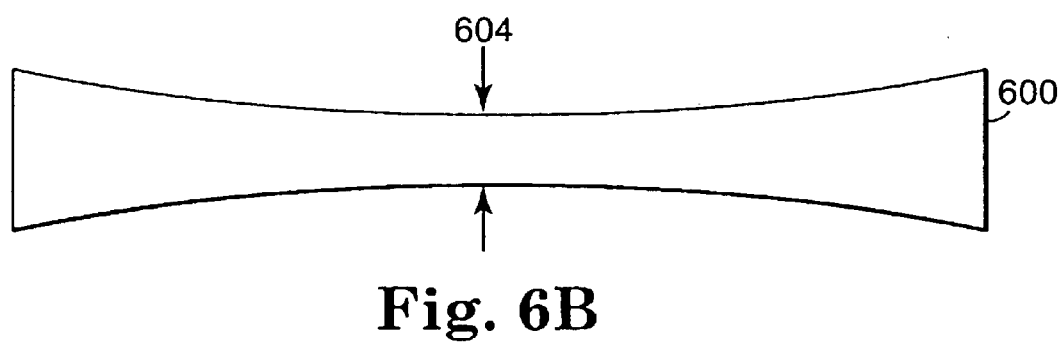

Referring to FIGS. 6A and 6B, a sling material 600 is shown in both the unstretched, condition (FIG. 6A) and in the tensioned condition (FIG. 6B). This sling material 600 can be comprised of any of the types and variations of mesh material previously discussed in this specification or any other type of mesh material that allows an elongation of the sling when placed under tension.

When in the unstretched condition (FIG. 6A) the sling 600 has a normal width 602 (e.g., approximately 5 cm) in the central region of the sling 600. When the sling 600 is placed into tension (FIG. 6B), however, the sling 600 takes on a reduced width 604 (e.g., approximately 1 cm) in the central region of the sling. By virtue of this phenomenon, a mesh material having certain known elongation (discussed above) properties can be used so that when the sling 600 achieves the reduced width 604, a known tension thus exists in the sling. Moreover, this known tension can be selected to exist in the range that is most optimum for treating the incontinence. Furthermore, by using a mesh material in accordance with previously discussed embodiments, the optimum tension can be achieved without the undesirable curling in the mesh that can cause tissue erosion. In the end, a mesh material is provided that potentially minimizes many of the undesirable aspects of placing a sling into a patient while at the same time optimizing the placement so as to enhance the prospect of successfully treating the incontinence condition.

Figure 7A:
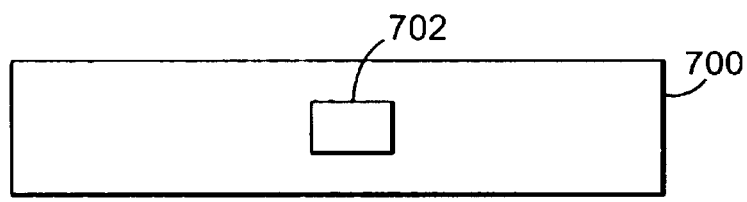
FIGS. 7A and 7B are views of a sling material in accordance with another embodiment of the present invention and a method of determining tension in accordance with the present invention; and, FIGS. 8A and 8B are views of a sling material in accordance with another embodiment of the present invention and a method of determining tension in accorance with the present invention.
Figure 7B:
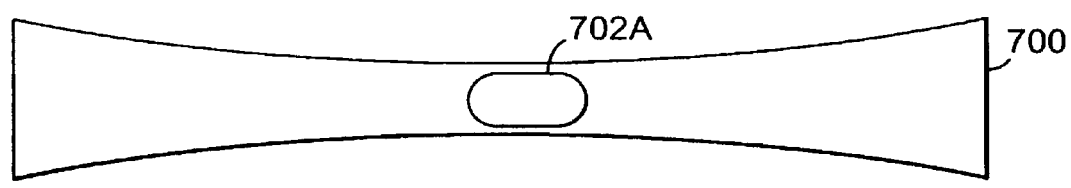

Referring to FIGS. 7A and 7B, another embodiment of a sling 700 that provides a visual tension indicia is disclosed. In this embodiment, the sling material is fabricated so that there is a geometrical pattern in the form of a square 702 visibly evident on the surface of the untensioned sling 700 (FIG. 7A). However, as the sling is placed in tension, the geometrical pattern 702 becomes distorted. Moreover, using the known elongation properties of the sling, the sling can be fabricated such that when the geometrical pattern achieves a different known shape due to tensioning, say, for example, a circle, ellipse or polygonal structure with one or more arcuate portions (e.g. 702A), the sling will have achieved the desired tension for proper placement in the patient.

The invention as disclosed in the embodiment of FIGS. 7A and 7B is not limited to visual indicia in the form of geometrical patterns. For example, the visual indicia could be a series of seemingly random lines that, under the target tension, become aligned into a straight line or into a geometrical pattern such as a triangle. As another example, the visual indicia could be a collection of marks or characters that, under the target tension, become aligned to spell a word such as "OK," or "STOP," or "LIMIT." In one embodiment the word could spell the manufacturer of the sling, such as "AMS."

The visual indicia described above could be integrated into the mesh material a variety of ways. For example, the mesh could actually be integrated into the fibers that are woven into the mesh so that the indicia is present upon weaving the material. In another example, the visual indicia could be added to the mesh as a component of a coating (e.g., silicone) applied to the mesh material.

Figure 8A:
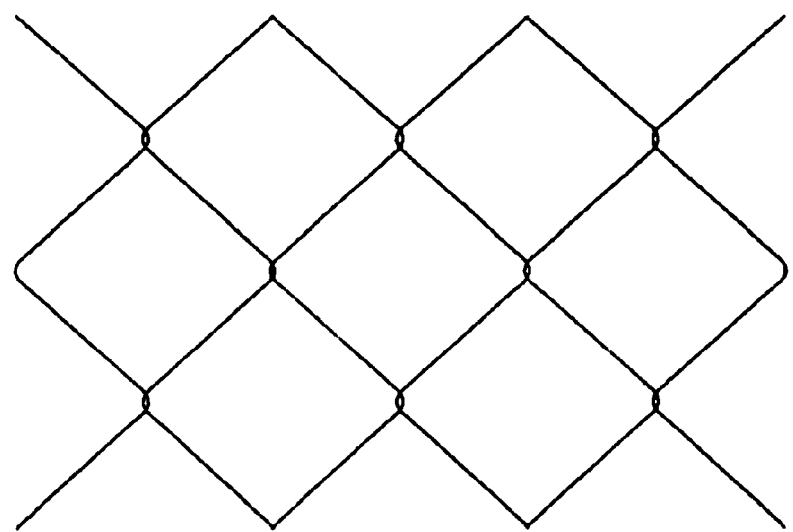
Figure 8B:
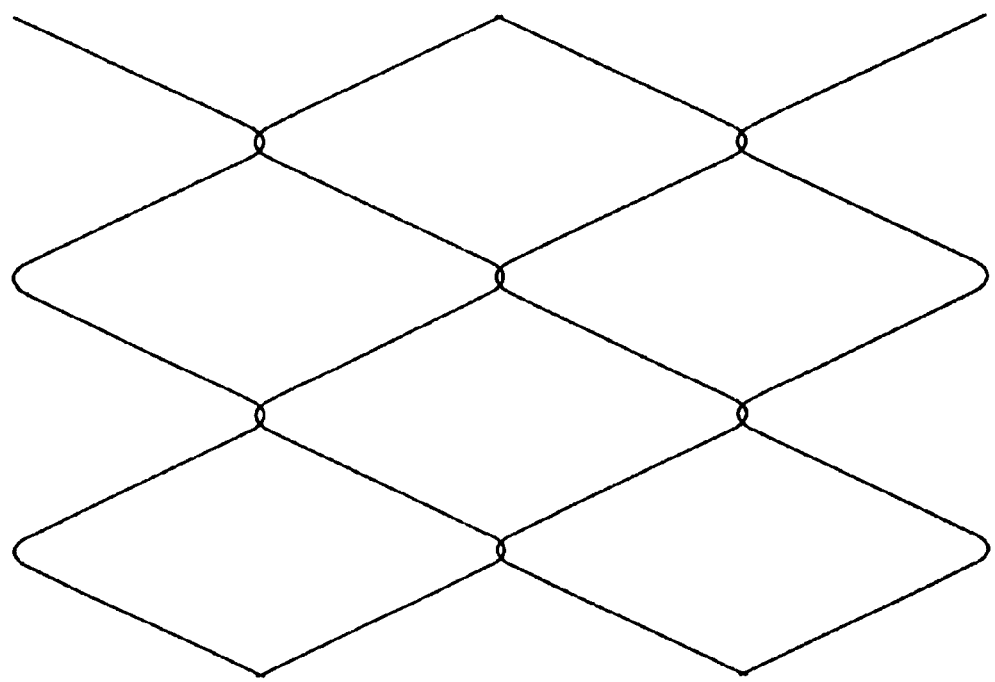

Referring next to FIGS. 8A and 8B, an embodiment of the invention is disclosed wherein the visual tension indicia is in the form of changes in the weave of the mesh. For example, a mesh 800 could be used such that it takes on a substantially square hole pattern (FIG. 8A) in the untensioned condition. Then, when the mesh 800 is stretched the hole pattern becomes distorted. Based on the known elongation properties of the mesh, the mesh can be manufactured such that a particular desired tension is present in the mesh when the hole material has changed into a different, recognizable pattern. In one embodiment, that new hole pattern could be a parallelogram structure as shown in FIG. 8B.

It will be evident to the reader that the visual tension indicia component of the present invention is not limited to the isolated embodiments disclosed in the figures and that various combinations of visual tension indicia is also contemplated. For example, a mesh using a varying hole pattern indicia as in FIGS. 8A and 8B could be combined with either of the visual indicia ideas contemplated in the embodiments of FIGS. 6A, 6B, 7A and 7B. In the end, the principle to guide the use of indicia is that the user be better enabled to know when a desired tension has been achieved in the sling by simple visual observation.

The present invention provides a simple, safe and stable system for treating urinary incontinence. The invention, as described herein, with reference to preferred embodiments, provides a coated sling that supports an abnormally distended urethra to effectively remedy urinary incontinence.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

All publications and patent applications in this specification are herein incorporated by reference to the same extent as if each individual publication or patent application was specifically and individually indicated by reference.

What is claimed is:

1. A sling for insertion into a patient comprising:
   a surgical sling adapted to support the urethra in its normal anatomic position and to prevent abnormal urethral descent under intraabdominal pressure;
   said surgical sling comprising a length of material having a longitudinal axis, and a latitudinal axis;
   wherein said material has a first elongation property along said longitudinal axis, and a second elongation property along said latitudinal axis,
   said first and second elongation property being different from each other, and
   wherein said second elongation property is greater than said first elongation property.

2. A sling for insertion into a patient comprising:
   a surgical sting adapted to support the urethra in its normal anatomic position and to prevent abnormal urethral descent under intraabdominal pressure;
   said surgical sling comprising a length of material having a longitudinal axis, and a latitudinal axis;
   wherein said material has a first elongation property along said longitudinal axis, and a second elongation property along said latitudinal axis,
   said first and second elongation property being different from each other, and
   wherein said first elongation property is approximately 8% elongation beyond a normal state of said sling material when said sling material is subjected to a tension of approximately 5 lbs.

3. The sling as set forth in claim 2, wherein said second elongation property is approximately 36% elongation beyond a normal state of said sling material when said sling material is subjected to a tension of approximately 5 lbs.

4. A sling for insertion into a patient comprising:
   a surgical sling adapted to support the urethra in its normal anatomic position and to prevent abnormal urethral descent under intraabdominal pressure;
   said surgical sling comprising a length of material having a longitudinal axis, and a latitudinal axis;
   wherein said material has a first elongation property along said longitudinal axis, and a second elongation property along said latitudinal axis,
   said first and second elongation property being different from each other, and
   wherein said first elongation property is in the range of approximately 24%–28% elongation beyond a normal state of said sling material when said sling is subjected to a tension of approximately 20 lbs.

5. The sling as set forth in claim 4 wherein said second elongation property is in the range of approximately 65%–75% elongation beyond a normal state of said sling material when said sling is subjected to a tension of approximately 20 lbs.

6. A sling for insertion into a patient comprising:
   a surgical sling adapted to be implanted in a tension free rest position to support the urethra;
   said surgical sling material comprising a length of polypropylene material having pores for promoting tissue ingrowth, a pair of major surface, a pair of ends and a pair of edges, and a longitudinal axis;
   wherein said polypropylene material has a central region with at least one major surface coated with silicone, the silicone coated central region being adapted to be placed adjacent the urethra to avoid tissue erosion, and end regions without silicone coating; and
   wherein said silicone coated polypropylene in the central region has a thickness within the range of approximately 0.024" (0.61 mm) to 0.036" (0.914 mm).

7. A sling for insertion into a patient comprising:
   a surgical sling adapted to support the urethra in its normal anatomic position and to prevent abnormal urethral descent under intraabdominal pressure;
   said surgical sling comprising a length of material having a longitudinal axis, and a latitudinal axis;
   wherein said material has a first elongation property along said longitudinal axis, and a second elongation property along said latitudinal axis,
   said first and second elongation property being different from each other,
   said material is coated with a substance that enhances biocompatibility, and
   wherein said first elongation property is in the range of approximately 19.5–21.5% elongation beyond a normal state of said sling material when said sling material is subject to a tension of approximately 20 lbs.

8. The sling as set forth in claim 7 wherein said second elongation property is in the range of approximately 120–130% elongation beyond a normal state of said sling material when said sling material is subject to a tension of approximately 20 lbs.

9. A sling for insertion into a patient comprising:
a surgical sling adapted to support the urethra in its normal anatomic position and to prevent abnormal urethral descent under intraabdominal pressure;
said surgical sling comprising a length of material having a longitudinal axis, and a latitudinal axis;
wherein said material has a first elongation property along said longitudinal axis, and a second elongation property along said latitudinal axis,
said first and second elongation property being different from each other,
said material is coated with a substance that enhances biocompatibility, and
wherein said first elongation property is approximately 2.5% elongation beyond a normal state of said sling material when said sling material is subject to a tension of approximately 5 lbs.

10. A sling for insertion into a patient comprising:
a surgical sling adapted to support the urethra in its normal anatomic position and to prevent abnormal urethral descent under intraabdominal pressure;
said surgical sling comprising a length of material having a longitudinal axis, and a latitudinal axis;
wherein said material has a first elongation property along said longitudinal axis, and a second elongation property along said latitudinal axis,
said first and second elongation property being different from each other,
said material is coated with a substance that enhances biocompatibility, and
wherein said second elongation property is approximately 65% elongation beyond a normal state of said sling material when said sling material is subject to a tension of approximately 5 lbs.

11. A sling for insertion into a patient comprising:
a surgical sling adapted to support the urethra in its normal anatomic position and to prevent abnormal urethral descent under intraabdominal pressure;
said surgical sling comprising a length of material having a longitudinal axis, and a latitudinal axis,
wherein said material has a first elongation property along said longitudinal axis, and a second elongation property along said latitudinal axis,
said first and second elongation property being different from each other,
said material is coated with a substance that enhances biocompatibility, and
wherein said first elongation property is approximately 10.5% elongation beyond a normal state of said sling material when said sling material is subject to a tension of approximately 5 lbs.

12. A sling for insertion into a patient comprising:
a surgical sling adapted to support the urethra in its normal anatomic position and to prevent abnormal urethral descent under intraabdominal pressure;
said surgical sling comprising a length of material having a longitudinal axis, and a latitudinal axis;
wherein said material has a tint elongation property along said longitudinal axis, and a second elongation property along said latitudinal axis,
said first and second elongation property being different from each other,
said material is coated with a substance that enhances biocompatibility; and
wherein said second elongation property is approximately 25% elongation beyond a normal state of said sling material when said sling material is subject to a tension of approximately 5 lbs.

13. A sling for insertion into a patient comprising:
a surgical sling adapted to support the urethra in its normal anatomic position and to prevent abnormal urethral descent under intraabdominal pressure;
said surgical sling comprising a length of material having a longitudinal axis, and a latitudinal axis;
wherein said sling comprises a plurality of regions along its longitudinal axis and wherein each region contain differing elongation properties from an immediately adjacent region, and
wherein said sling material has a coated central region having an increased longitudinal elongation property and a somewhat decreased latitudinal elongation property as compared to elongation properties of said central region in a normal state.

14. A sling as set forth in claim 13, wherein said sling material has a coated intermediate region on either side of said central region, each of said intermediate regions having a decreased longitudinal elongation property and an increased latitudinal elongation property as compared to elongation properties of each of said intermediate regions in a normal state.

15. A sling as set forth in claim 14, wherein said sling material has a coated end region adjacent each intermediate region, each of said end regions having a decreased longitudinal elongation property and an increased latitudinal elongation property as compared to elongation properties of each of said end regions in a normal state.

16. A sling according to claim 6 wherein the pores of the polypropylene material in the central region remain open and clear of silicone.

17. A sling according to claim 6 wherein said polypropylene comprises non-knitted polypropylene fibers.

18. A sling according to claim 17 wherein said non-knitted polypropylene fibers are multidirectional.

* * * * *